United States Patent [19]

Olsson et al.

[11] Patent Number: 5,387,204
[45] Date of Patent: Feb. 7, 1995

[54] METHOD AND APPARATUS FOR DOSING AN ADDITIVE AT COLLECTION OF LIQUID

[75] Inventors: Per Olsson; Lennart Strömberg, both of Stockholm, Sweden

[73] Assignee: Medical Projects HB, Saltsjobaden, Sweden

[21] Appl. No.: 94,007

[22] PCT Filed: Oct. 22, 1993

[86] PCT No.: PCT/SE92/00048

§ 371 Date: Jul. 27, 1993

§ 102(e) Date: Jul. 27, 1993

[87] PCT Pub. No.: WO92/13582

PCT Pub. Date: Aug. 20, 1992

[30] Foreign Application Priority Data

Feb. 1, 1991 [SE] Sweden ............................ 9100326

[51] Int. Cl.$^6$ .............................................. A61M 1/00
[52] U.S. Cl. ...................................... 604/317; 604/118
[58] Field of Search .......................... 604/317, 118, 119

[56] References Cited

U.S. PATENT DOCUMENTS

| | | |
|---|---|---|
| 3,783,866 | 1/1974 | Tirkkonen . |
| 4,191,181 | 3/1980 | Franetzki et al. . |
| 5,024,613 | 6/1991 | Vasconcellos et al. ............... 604/4 |
| 5,098,372 | 3/1992 | Jonsson ............................ 604/4 |
| 5,234,403 | 8/1993 | Yoda et al. ......................... 604/4 |

Primary Examiner—Jerome L. Kruter
Attorney, Agent, or Firm—Larson and Taylor

[57] ABSTRACT

A method and a device designed to suck and to convey various types of liquids through a suction hose (45) and at the same time does (4) an additive to the liquid in an accurate proportion to the amount of the sucked liquid. A liquid or a liquid/air/gas mixture is sucked by means of a suction nozzle (2,45), which is influenced by a certain pressure P2 with a moderate suction action, and is passed through the suction hose (45). A dosage device (4), which includes a flexible dosage container (20), which is enclosed in a rigid casing (21), and which is influenced by a certain relatively lower pressure P3 (providing a stronger suction action) than the pressure in the suction hose (45), is connected directly to the suction hose (45). The pressure gradient P2-P3 is adjusted in such a way that no additive is introduced when only air/gas is sucked through the suction hose (45), whereas an additive does flow into the suction hose (45) as soon as some amount of liquid is sucked through the suction hose, and the amount of dosed additive is proportional to the amount of sucked liquid. The suction hose (45) may be connected to a separation and defoaming filter (3), which in its turn may be connected to a de-air receiver (5) with a mechanism designed to de-air the sucked liquid as well as to store the liquid without any admixture of gas/air.

20 Claims, 4 Drawing Sheets

METHOD AND APPARATUS FOR DOSING AN ADDITIVE AT COLLECTION OF LIQUID

FIELD OF THE INVENTION

The present invention generally relates to a method and a device designed to, without air or gas admixture, collect and/or convey various types of liquids, to be stored in a closed air free/gas free package or receiver or to be directly fed into another liquid system, without any contact with human hands and without any risk of contamination during the operation and preferably under sterile conditions.

The invention can be used when handling various types of liquids and for many purposes, particularly when handling liquids, which easily are damaged, oxidized, gelled etc., i.a. due to influence of air or other gases, liquids which tend to foam when handled, liquids which contain not desirable or harmful particles or impurities, mixed liquids which tend to separate or form layers etc., during or after the collection.

The method and the device can be used e.g. when food-stuffs such as milk, cream, oils, fruit drinks, juices etc. are handled, when corrosive or hazardous liquids of various types are handled, when it is important that the liquid will not contact human skin or be discharged into the environment or into drains, when oils are handled or liquid mixtures which are mutually insoluble are handled, when blood is handled in connection with medical surgical operations, when various types of waste liquors etc. are sucked.

The invention was developed particularly in connection with the handling of blood, and it will in the following text mainly be described in connection with such a handling.

BACKGROUND OF THE INVENTION

Blood is always a liquid in short supply and large amounts of blood are used during blood transfusions, e.g. in connection with surgical operations. Blood is expensive to collect, to test as well as to store. There is also a risk of transmission of jaundice, HIV-infection and other diseases during blood transfusions.

In connection with certain operations the patient may lose large quantities of blood, sometimes as much as several liters. This blood normally is wasted and the patient has to receive the corresponding amount of blood through transfusions.

The problem of supplying blood has to some extent been solved in various ways. There are e.g. methods of purifying and anticoagulation-treating blood, which has been partially coagulated, but these methods are expensive and time-consuming, and the transfusion product is inferior. Also. autotransfusions are used now, a patient letting his own blood as a blood-donor a few weeks before a planned operation, the patient, in case a need arises, having his own blood restored during or subsequent to the operation. However, this method needs planning and cannot be applied when emergency operations are needed. Normally, the patient also must be reasonably healthy, when he is a blood-donor, and equipment for possible purification, catalogueing and storage of the patient's blood is required. This method has so far only been sparingly used.

Consequently, the basis of the invention, according to the last mentioned aspects of blood treatment, has been the idea of trying to collect and autologously inject in the patient as much as possible of his own blood, which is removed from his blood vessel system during the operation.

Four main problems arise when doing this:

When blood is sucked from a wound surface, large amounts of air or another gas or a gas mixture inevitably are sucked jointly with the blood, which results in an air admixture with a strong frothing, which like the contact of the blood with foreign substances and free air contributes to an initiation of the mechanisms, which lead to an activation of the coagulation system of the blood as well as alterations of or in the cells of the blood;

When blood is stored in some type of storage unit, air or another present gas as well as froth will be dominant in the storage unit, which accelerates the coagulation and besides prevents a direct return of the blood to the patient, partly due to the air contents itself and partly also due to the fact that the enzyme system and the cells of the blood are activated by the interface between blood and air bubbles;

The collected material may contain not desirable tissue fragments from the operation wound (clots, muscle, fat, bone etc.), which activate the enzyme system of the blood; this activation as well as the admixture of not desirable and in this connection dangerous tissue fragments prevent a direct return of the collected blood to the patient; and The collected blood may be infected and consequently it will be clearly inappropriate to return the blood in this condition to the patient.

SUMMARY OF THE INVENTION

The above-mentioned problems can be solved according to the present invention with a method and a device, by means of which the patient above all is injected with his own blood, which he has bled from his own blood vessel system due to a tissue injury and/or during the operation (autologous transfusion) and which blood has been sucked in connection with the operation, by means of which:

The blood which disappears during the surgical operation is sucked continuously;

The sucked blood/air/gas-mixture receives automatically and in proportion to the amount of sucked blood an admixture of an anticoagulant agent, e.g. a citrate of a type which is active and known per se, of a disinfectant or of any type of blood preserving agent, controlled by a differentiated pressure in the system;

The blood/air/gas mixture is caused, in a closed system, to pass a defoaming and separation filter, in which the blood froth is disintegrated and not desirable particles are separated, whereas the blood is allowed to pass;

The blood flows into a receiver, in which the blood is allowed to slowly flow downwards along the walls of the receiver or along inclined planes mounted in the receiver, whereas air bubbles included in the blood are allowed to escape to the upper part of the receiver;

The blood is collected in the lower part of the receiver, which in its bottom is provided with a valve, which opens up when a certain amount of blood has been collected in the bottom of the receiver, the blood flowing into a collecting vessel, said valve closing again when the blood level in the lower part of the receiver has been lowered to such an extent, that there may be a risk that air and gas will follow the blood into the collecting vessel; and The collection of the blood in the vessel is done entirely without any admixture of air or any other gas by means of a certain negative pressure, which acts on a completely air-void flexible container, and the suction of air from the upper part of the receiver is done by means of a suction system with a negative pressure, which is higher (more negative) than the pressure on the flexible collecting container and the pressure on a container for the anticoagulant.

It is common practise, when blood is collected in bottles or flexible bags, to add an anticoagulant, e.g. a citrate, and this usually is done by dosing in advance a certain amount of citrate solution in the blood bag, calculated according to the amount of blood which the bag is to contain, the citrate being mixed with the introduced blood. The amount of citrate solution ought to be proportionate to the amount of blood. However, the amount of filled blood may vary, and in case a smaller amount of blood is filled in the blood bag than what had been estimated, then the citrate contents in the blood bag would be higher than what is needed.

Also, the citrate admixture ought to be done as quickly as possible subsequent to the blood collection, and this is particularly true, when wasted blood from surgical operations etc. is sucked, and suitably it ought not to be delayed, until the filtrated and de-aired blood finally has been collected in the blood bag. In case the blood, in an immediate connection with the sucking, is returned to the patient's own blood system, then the admixture of the citrate solution and possibly also a disenfectant must also be done in close direct connection with the sucking of the blood.

Thus, according to the invention a dosage of one or several additives to the sucked liquid is done, in the last described case to blood, in close connection with the sucking place, and preferably in a place before the liquid arrives to the means of filtering and de-airing of the liquid (the blood). The dosage device for additives is according to the invention designed in such a way, that the same in a simple way will yield a surprisingly accurate proportionate dosage in relation to the amount of sucked liquid.

This is done by subjecting the dosage device and the suction nozzle for the sucking of liquid to negative pressures at different negative pressure levels, the pressure gradient between these different pressure levels being calculated in such a fashion, that no additive at all will be introduced, when no liquid is present in the suction nozzle and that the amount of dosed additive will be almost completely proportionate to the amount of sucked liquid.

BRIEF DESCRIPTION OF THE DRAWINGS

Characterizing features and advantages of the present invention will be set forth in the following detailed description of an embodiment of the invention, which is illustrated in the accompanying drawings.

In the drawings

DETAILED DESCRIPTION OF THE PREFERRED EMBODIMENT

The device shown in FIG. 1 comprises 6 main parts, which operate with a certain pre-set pressure gradient, namely a main negative pressure P3 (suction), which acts on some of the parts, and a certain higher pressure P2 (relatively lower suction action), which acts on other parts of the device, which will be explained in the following text, as well as a third additional higher pressure P1, which can be the atmospheric pressure and at which the liquid or the liquid/air/gas mixture is sucked into the device.

Figure 1:
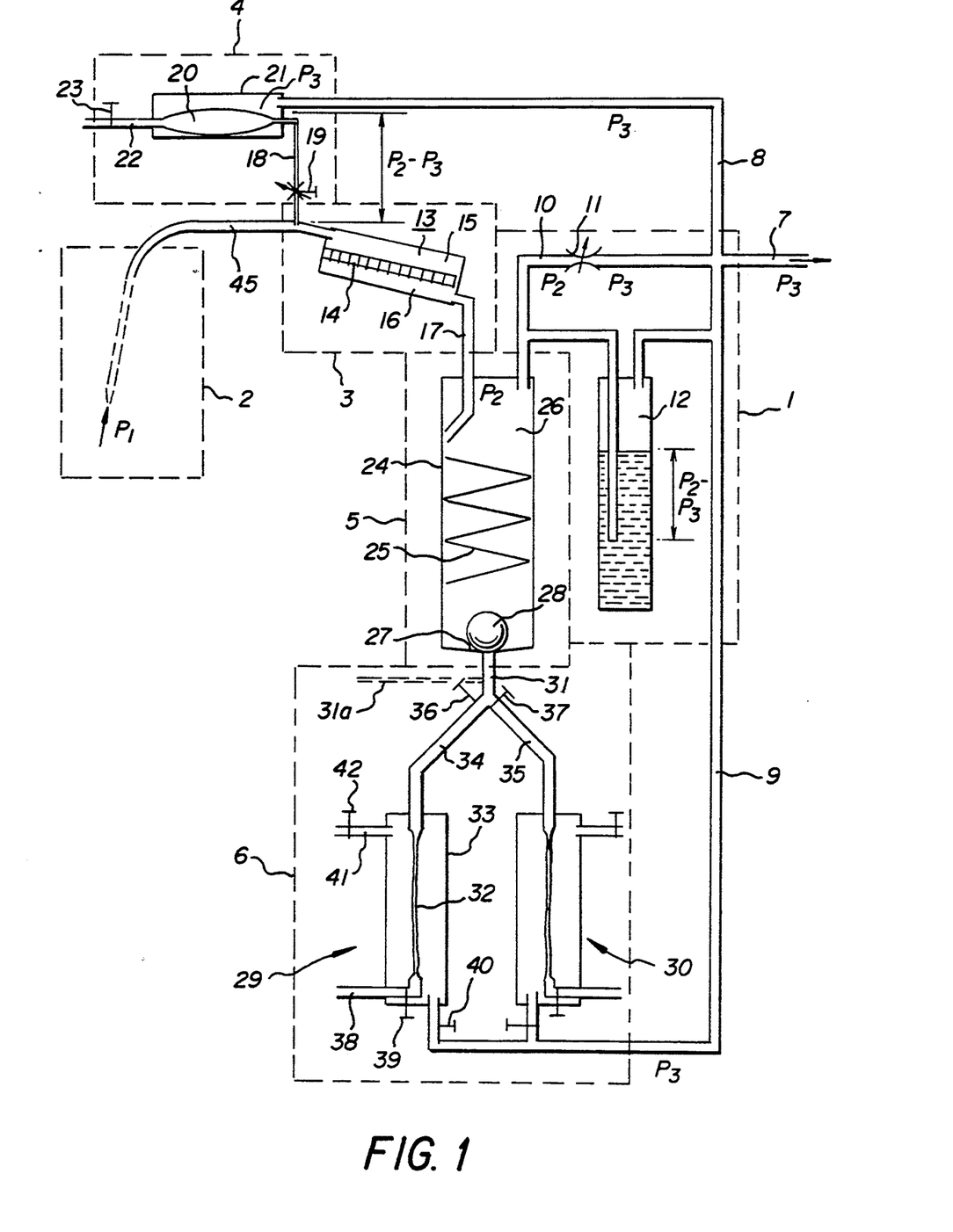
FIG. 1 shows schematically and substantially simplified a device designed to carry out the method according to the invention, shown before the device is used to collect a liquid.

The main parts of the device have in FIG. 1 been indicated as blocks with dashed lines, although the parts can be completely or partially integrated to a continuous disposable device. The parts are as follows:

1) A suction system with means to obtain negative pressures at two different-pressure levels, e.g. a suction source, with a pilot valve and a manometer or pressure gauge, designed to obtain a negative pressure with a lower pressure level P3 and a higher pressure level P2 and connected to the various parts of the device by means of conduit systems and designed to suck a liquid under an additional higher pressure P1;

2) A suction nozzle designed to suck a liquid at an atmospheric or normal pressure P1 and which is influenced by said relatively high pressure level P2;

3) A separation and defoaming filter, which is connected to the suction nozzle and which is influenced by the relatively higher pressure level P2;

4) A device designed to dose one or several types of admixture agents for the liquid, e.g. antioxidation additives, anticoagulants etc., which agents are influenced by the lower pressure level P3;

5) A receiver with walls or inclined planes, along which the liquid will flow downwards, and provided with means designed to de-air the liquid and with a bottom valve designed to drain the liquid and influenced by pressure at the higher pressure level P2; and 6) Means designed to recover the filtrated and vented liquid by transferring the liquid directly to another liquid system or a system with one or several collecting vessels, directly connected to receiver 5 and influenced by a pressure at lower pressure level P3 as well as provided with means designed to drain the receiver or receivers.

Suction system 1 comprises a pipe or a hose 7, which is connected to a suitable negative pressure source P3 (not shown), which can be any conventional or available negative pressure source or which can be an air ejection pump or the like. Conduit 7 is through a first branch conduit 8 connected to dosage device 4, through another branch conduit 9 to a certain part of collecting vessel 6 and through a third branch conduit 10 to de-air receiver 5 via a pilot valve 11, which controls the gas flow in this branch conduit and consequently also in receiver 5 to a predetermined extent, i.e. to obtain a higher pressure P2 (suction action lower) in receiver 5 than in those parts which are influenced by pressure P3.

In order to be able to preset and read pressure gradient P2-P3 a manometer or pressure gauge 12 is connected between the conduits having pressures P3 and P2 respectively. In the illustrated case the manometer is a water seal manometer, the pressure gradient being measured in mm water column, but it can just as well be any type of manometer or water gauge. Pressure gradient P2-P3 is controlled by setting the pilot valve and is adjusted in such a way, read on the water seal or the manometer, that an automatically acting bottom valve in receiver 5 normally is closed and opens up only when a certain liquid volume is obtained in the lower part of receiver 5 and closes before the liquid level in the receiver has decreased so much that a risk exists that air or another gas or a gas mixtures will pass the valve. The upper and the lower limits of pressure gradient P2-P3 is a very important factor for the function and the safety of the device. The water seal or a similar device used instead is a guarantee for a reliable control of pressure gradient P2-P3.

The artisan knows very well that the two different negative pressures P3 and P2 respectively, can alternatively be obtained from two external negative pressure sources for the different pressure levels, pilot valve 11 being left out and pressure P2 of the higher pressure level being propagated directly into conduit 10 to venting receiver 5.

Suction nozzle 2 can be any known nozzle, designed to suck a liquid in the open air or in any other gas or in a gas mixture. The nozzle is connected to de-air receiver 5 via separation and defoaming filter 3 and acts with pressure P2, possibly reduced to some extent due to the restriction, which may exist in filter 3.

Separation and defoaming filter 3 comprises a closed container 13 with a filter insert 14 mounted therein of a type which is capable of partly filtering particles, tissues etc. from the liquid and partly disintegrating foam by separating air from blood in the foam, when the liquid passes through the filter. Filter insert 14 divides up the container into two parts, an upper container part 15, designed to collect foam and particles and a lower part 16, from which the liquid flows to de-air receiver 5. Suction nozzle 2 leads to upper container part 15, and an outlet or connection tube 17 from lower container part 16 leads to receiver 5. Filter 13 suitably is mounted slightly downwardly inclined towards outlet tube 17. Higher pressure P2 acts in filter 13 and is transmitted via connection tube 17 from the upper part of receiver 5.

The separation and defoaming filter alternatively can be enclosed as an integral interior part of the de-air receiver and can be designed as a downwardly widening filter funnel, through which the liquid is sucked, and a lower funnel, which leads the liquid to the walls of the container or the filter can be designed as a filter cylinder, which is mounted concentrically inside the receiver and which is sealingly connected to the receiver's upper and lower parts.

At a certain position between suction nozzle 2 and filter 13 a dosage device 4, or several dosage devices, mutually connected in parallel, is mounted on a higher level than suction nozzle 2 and filter 3 and connected to suction nozzle 2 through a connecting tube 18 with a pilot valve 19, by means of which the flow of dosage medium can be regulated. The dosage device comprises a flexible container or a bag 20, which is enclosed in a rigid casing 21, which via branch conduit 8 is influenced by lower pressure P3. Container 20 can be filled through a conduit 22 with a stop valve 23. The pressure between casing 21 and container 20 is lower than the pressure in suction nozzle 2, and this results in a suction action on the dosage medium, which corresponds to a pressure gradient P2-P3. This suction action prevents dosage medium from flowing from bag 20 into suction nozzle, until the pressure in suction nozzle 2 decreases, and this occurs when a liquid in the form of liquid drops or as a liquid column N (see FIG. 2) enters the nozzle and stops a free entry of air into the nozzle, pressure gradient P2-P3 decreasing so much, that the dosage medium, due to the gravitation, can flow downwards through hose 18. Consequently, in this situation the dosage medium flows into the suction nozzle and is mixed with liquid. The amount of dosage medium which is mixed with the liquid is proportionate to the amount of sucked liquid.

Three different situations can be distinguished:

Situation 1 The device solely sucks air/gas mixture:

Pressures P2 and P3 have been set, the device sucking only an air/gas-mixture through suction hose 45. Pressure P2 is higher than P3 and a suction force acts on liquid column N, which is as large as pressure gradient P2-P3. This suction force prevents dosage medium from flowing through hose 18 and into suction hose 45. The height of liquid column N, which corresponds to the distance between the upper point in the container and the level of the point where hose 18 is connected to suction hose 45, is adjusted to the set pressure gradient P2-P3 or vice versa, an equilibrium being obtained between pressure gradient P2-P3 and the flow resistance in hose 18 on one side and the gravitation, which strives to let the liquid column in hose 18 flow downwards into hose 45 on the other side.

Situation 2 Liquid and gas/air is sucked through suction hose 45:

In this situation the air flow through suction hose 45 is stopped, since the sucked liquid reduces the passage of the air/gas. Pressure P2 is reduced in this way and approaches pressure P3. P3 is constant and independent of the flow in hose 45. This means that the equilibrium is disrupted and the value of pressure gradient P2-P3 decreases, and the suction action upwards on liquid column N in hose 18 decreases also, dosage liquid due to the gravitation being able to flow downwards in hose 45 with an amount which is determined by the existing not balanced pressure gradient P2-P3.

Situation 3 The device solely sucks liquid:

Only liquid is sucked through suction hose 45 and thus no air/gas flow exists through suction hose 45. P2 will in this case be almost as low as P3 and pressure gradient P2-P3 approaches zero. In this way a maximum and free flow of dosage liquid through hose 18 and into suction hose 45 is obtained. The flow in hose 18 is counteracted to a larger or lesser extent by the flow resistance in hose 18 and the setting of pilot valve 19. The flow resistance in hose 18 can be changed manually or by means of some type of automatic mechanism.

In the embodiment of the invention, in which the device is used to collect blood, the dosage medium can e.g. be a so called citrate solution, which as the artisan knows is used to bind the ionized calcium in the blood and in this way prevent the coagulation of the blood. The dosage medium also contains a disinfectant. Also, it is possible to mount two or several dosage devices in parallel with each other in order to dose citrate solution as well as the disinfectant and possibly other agents. The additive can be a liquid, a gel, a powder etc., provided it can be caused to flow into suction hose 2 and be mixed with the sucked liquid. Thus, the additive can be any agent or a mixture of agents having an active influence on the sucked liquid or designed to facilitate the disintegration of the foam or with any other functions.

The dosage medium can be used for many purposes, e.g. adding vitamins to liquid food products, adding emulsifiers to oil/water-mixtures and many other purposes.

De-air receiver 5 comprises a closed container unit 24, in the upper part of which connection tube 17 for the liquid ends and which is provided with a system of inclined planes 25, on which the liquid can slowly flow downwards, the air which is mixed with the liquid having a chance to escape to upper part 26 of unit 24. The inclined plane can be a system of inclined plates or a spiral-shaped track or preferably it is a helical tube or a helically arranged flexible hose having such a dimension that the liquid merely fills a portion of the cross-section, the air having a chance to escape upwards. Also, it is possible to lead the liquid towards the walls of the receiver and thereby let it flow downwards along the walls, and the receiver can for this purpose of course also be made slightly convergent. In the upper part of the container branch conduit 10 also ends, which constitutes an exhaustion tube for air, which can escape directly outward through pilot valve 11 and suction hose 7.

In the bottom of container unit 24 there is a valve seat 27, in which a type of valve cone seals, which in the shown embodiment is a displacement valve ball 28. Valve ball 28 is designed with such a mass and such a lifting force in relation partly to the pressure in the evacuation conduit 10 and partly to the pressure from the outlet of the receiver, that it will open up, when a certain amount of liquid column has been collected on the bottom of the receiver and will close, before the liquid column has been drained completely. The risk that air will be sucked through the valve seat and into the collecting container or containers 6 will be eliminated in this way.

The bottom valve in the receiver can be a type of manually or automatically actuated valve. In case the liquid will be directly transferred to another liquid system, e.g. when citrate-treated, filtrated, defoamed or de-aired blood will be directly restored to the patient, the valve can be a manual valve and can be connected to a hose or a conduit 31a, as is shown schematically in the drawings.

The valve alternatively can be an electrically, pneumatically or hydraulically actuatable stop valve, which is operationally connected to an electric, optical or capacitive level sensor, which is mounted inside or outside the receiver and which opens up and closes the valve for a certain predetermined high and low respectively liquid level in the receiver.

In the illustrated case the device is designed with two liquid containers 29 and 30, connected in parallel, which are identical and connected to receiver 5 through a drain conduit 31, which starts at valve seat 27. Each liquid container contains a flexible bag 32, which is enclosed in a shape-permanent casing 33. Bag 32 is with its upper part directly connected to drain conduit 31 via a branch conduit 34,35 with a stop valve 36,37. The lower part of bag 32 has a drain conduit 38 with a stop valve 39. The shape-permanent casing 33 is connected to branch conduit 9 via a stop valve 40, which when it is opened up gives the space between casing 33 and bag 32 the lower pressure P3 and thereby causes a suction action on the bag and a suction downwards of liquid from receiver 5, when its bottom valve 28 is opened up. Shape-permanent casing 33 has a second tube joint 41 with a stop valve 42 in order to give the space between casing 33 and bag 32 a positive pressure in order to remove all the air from bag 32, which in FIG. 1 is shown in its flat compressed air-void condition, which is the starting point for liquid suction.

Figure 2:
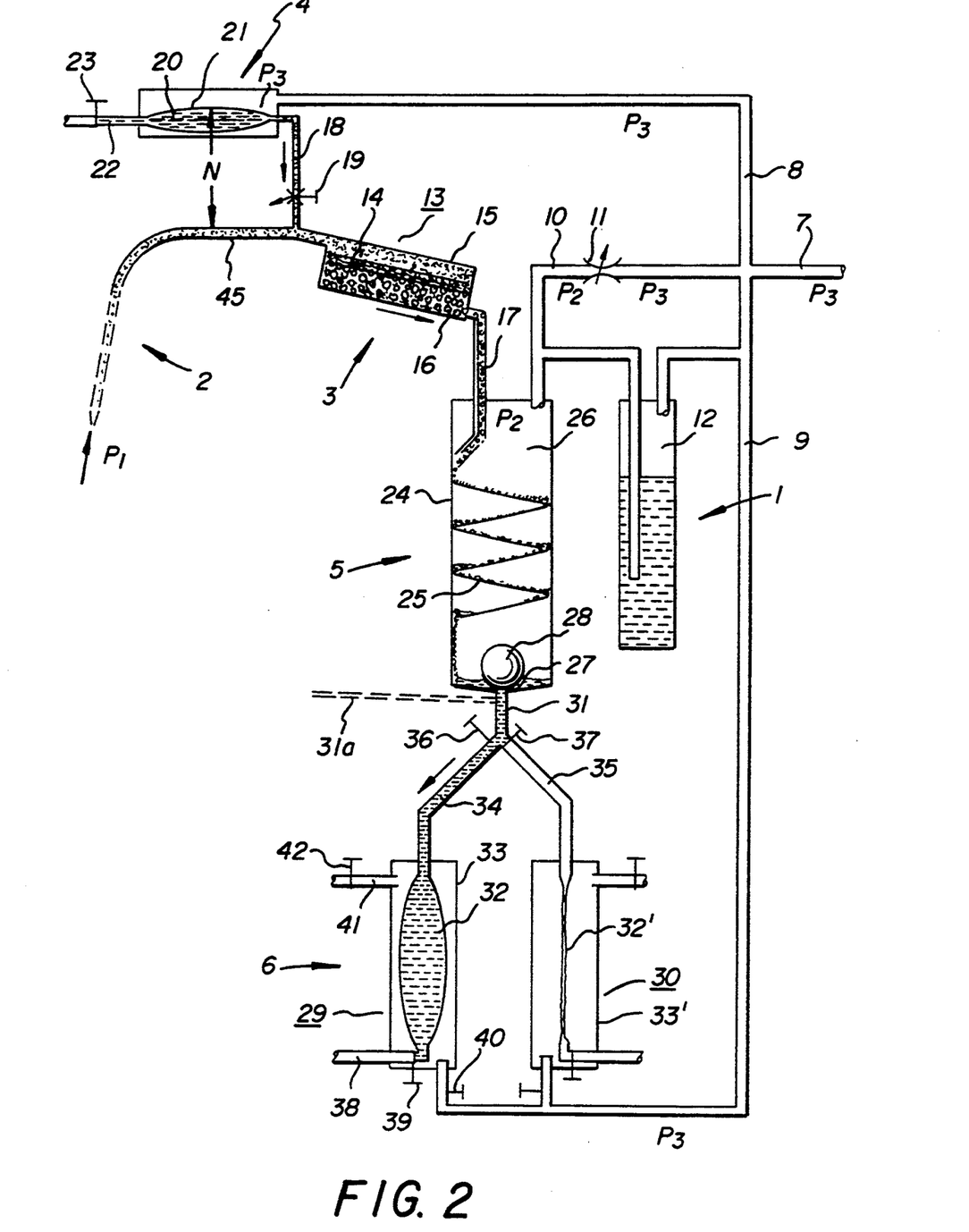
FIG. 2 shows the device according to FIG. 1 in operation during the liquid collecting.

FIG. 2 shows the device in FIG. 1 when used to suck a liquid, e.g. blood, through suction nozzle 2. The function is as follows:

Suction hose 7 is connected to a source of negative pressure P3, which pressure is propagated through branch conduits 8 and 9 to dosage device 4 and to collecting vessel 6 respectively. Via pilot valve 11 a higher pressure P2 is propagated to receiver 5 and via the latter also through separation and defoaming filter 3 to suction nozzle 2, in which a pressure is obtained, which is at least approximately the same as pressure P2.

Valve 36 to the one container bag 32, the left bag in the drawings, is opened up and valve 40 to container casing 33 is opened up, a pressure P3 being obtained between bag 32 and casing 33.

It is assumed that pilot valve 19 to dosage device 4 in advance has been set in such a way, that low pressure P3 in dosage device 4 prevents dosage liquid from flowing into conduit 45 between suction nozzle 2 and filter 13, in case the suction nozzle does not contain any liquid. When liquid is sucked into conduit 45 between suction nozzle 1 and filter 3 pressure P2' decreases in this conduit and this results in a decrease in pressure gradient P2'-P3, which approaches 0, dosage agent in a certain amount in proportion to the amount of liquid sucked from suction nozzle 2 flowing downwards through conduit 18 and into suction hose 45 and further into filter 13. The device is then ready to be used.

Suction nozzle 2 is lowered towards the liquid to be sucked. The liquid must be influenced by a pressure P1, which is higher than pressures P3 and P2, and generally the liquid is influenced by the atmospheric pressure in the open air. Usually a mixture of air and liquid drops or a continuous liquid column is sucked into nozzle 2. In case nozzle 2 and suction hose 45 contain liquid, the free air stream through the nozzle is stopped and the pressure decreases (the suction action increases) in hose 45 to filter 3, and this means that pressure P2' approaches the value of counter pressure P3 on flexible container bag 20, and that dosage agent, e.g. a citrate solution, flows into suction hose 45 and is mixed with the sucked liquid, e.g. blood.

It was surprising to find that the amount of dosed additive will be roughly proportional to the amount of liquid, which is sucked through suction hose 45, and this is true regardless of how large or small the amount of sucked liquid is and how the liquid is mixed with air/gas, with a large amount of air/gas, with a small amount air/gas or possibly with no amount of air/gas. Consequently, it is possible to obtain an accurate dosage of the additive, which dosage can be varied by setting the pilot valve and above all by adjusting pressure gradient P2-P3.

The simplest embodiment of the present invention only comprises a suction device 2, which is influenced by a certain relatively high pressure P2 (a low suction action) and a dosage device 4, which is influenced by a certain relatively low pressure P3 (a strong suction action) and comprises a suction nozzle 2 with a suction hose 45, container 20 of dosage device 4 through its connection joint 18 being connected to suction hose 45 in the way described above, and suction hose 45, as seen in the flow direction downstreams of the point where dosage device 4 is connected, ending directly in a collecting vessel. The most important feature of the invention resides in that fact that dosage device 4, thanks to the pressure difference between the two negative pressures P2 and P3, i.e. pressure gradient P2-P3, yields an amount of dosage agent to the liquid, which is sucked through suction device 2, which amount with a surprising accuracy is proportional to the amount of sucked liquid, regardless of how large or small the amount of air or gas is, which is sucked jointly with the liquid. As is mentioned above, the device can be used in a plurality of various technical situations.

The liquid is sucked along into separation and defoaming filter 3, in which tissue particles, e.g. clots, muscle particles, bone particles and fat etc. are separated on the upper side of filter insert 14 and in which simultaneously also a disintegration of blood froth takes place, which maybe has been formed, when the air/gas/liquid mixture passed through the suction nozzle and hose 45 up to filter 13, whereas the liquid passes through filter insert 14 and flows into the receiver through conduit 17. The liquid is then allowed, due to its own gravitation, to slowly flow downwards along the inclined plane(s) 25 or along the walls of the receiver, the air which has come along with the liquid into receiver 5 and the air bubbles which are included in the liquid being allowed to be separated. The air escapes from the upper part 26 of the receiver through de-air conduit 10, which is influenced by the higher pressure P2 and then out through suction hose 7. Liquid is collected successively in the lower part of the receiver.

When the liquid has reached a certain predetermined volume valve ball 28 is lifted and liquid is sucked through the influence of pressure P3 on container bag 32, which pressure is lower than pressure P2 in the receiver, downwards into container bag 32.

When the liquid level in receiver 5 has been lowered to a predetermined level, set in order to prevent a stream of air into drain conduit 31 and container bag 32 or into hose 31a, valve ball 28 closes again, balanced partly by the mass of the ball and partly by pressure gradient P2-P3, and a new unit volume of liquid is collected in the same way on the bottom of the receiver.

In case bag 32 in one of the liquid containers will be full, valves 36 and 40 are closed and the corresponding valves in the other, the shown right-hand liquid container are opened up, this second container being filled with liquid in the same way. Filled liquid bag 32 can be emptied in a handling bag, and the liquid be directly fed to the patient, possibly via a blood processor or to a cold storage device, to be used at a later date. When a so called heart-lung-machine is used, the collected blood can with advantage be directly transferred to the vein reservoir of the machine and from this reservoir to the patient. Filled bag 32 in the collecting vessel can be emptied through gravitational flow, but the drainage can also be done by applying a positive pressure in the chamber between casing 33 and bag 32 via connection 41.

As is known, a contact with foreign substances such as walls in flow conduits and apparatuses may activate the cells of the blood and its enzyme system, e.g. the coagulation system and the cells of the blood, which will strongly and harmfully affect the quality of the blood. In order to eliminate these problems when treating blood by means of the described device at least some of the walls in suction nozzle 2, suction hose 45, filter 3, connection tube 17, container 24 as well as on inclined planes 25 can be provided with a coating of an agent, which does not affect the liquid, e.g. a resistant heparin, which is capable of inhibiting the mechanisms, which activate the coagulation system of the blood as well as changes of or in the cells of the blood. Several heparinizing methods and similar methods are known, one of them being protected i.e. by European patent No. 86.186.

In order to achieve a satisfactory result, when a citrate solution is dosed in blood, the dimensions of connection tube 18 of the citration device, the setting of pilot valve 19 and above all pressure gradient P2-P3 suitably can be selected in such a way, that citrate bag 20 doses an amount of citrate solution, which is equal to 8–20% of the amount of blood, which flows into suction nozzle 2 and through suction hose 45.

Figure 3:
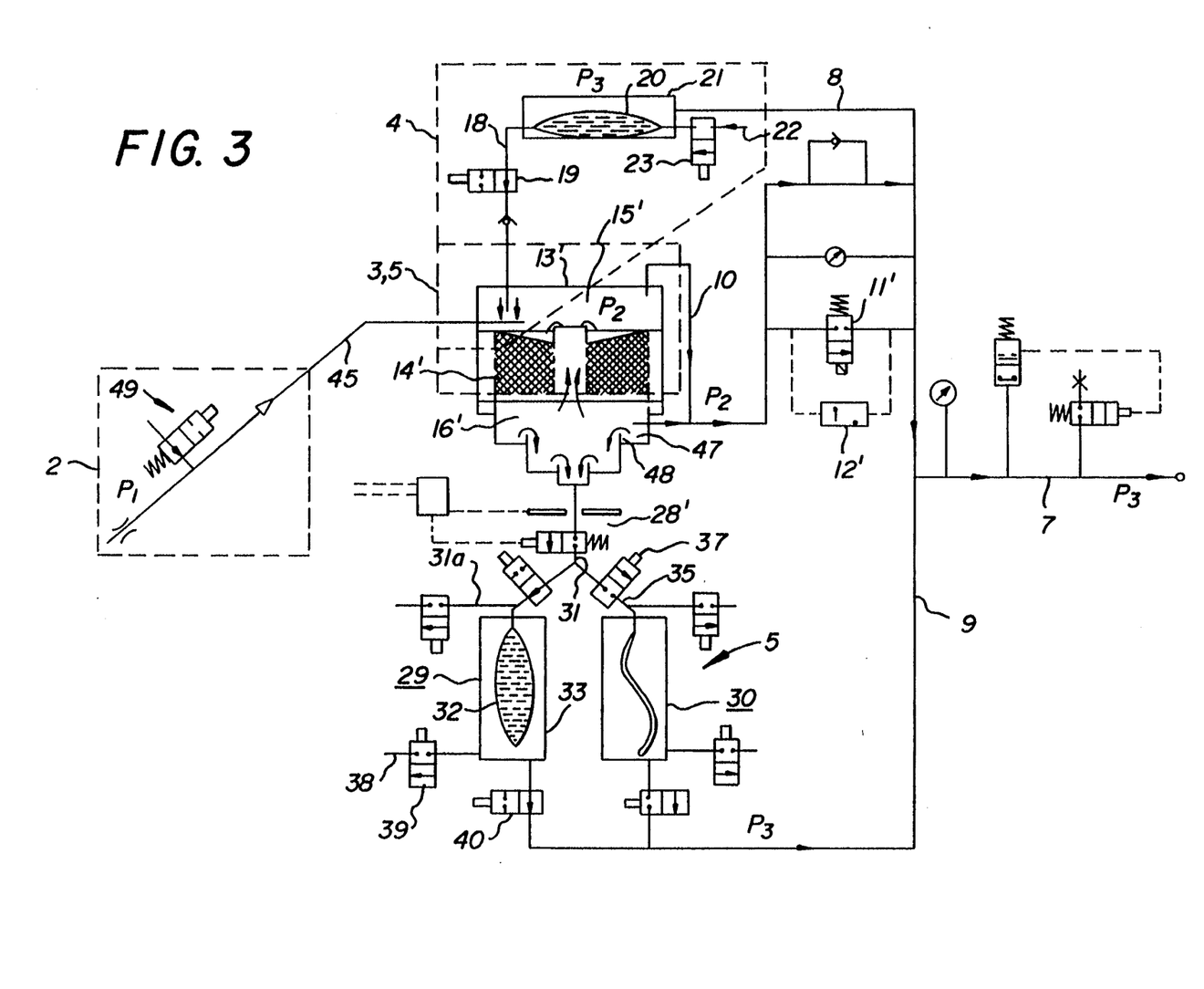
FIG. 3 is a modified embodiment of the device of the invention.
Figure 3A:
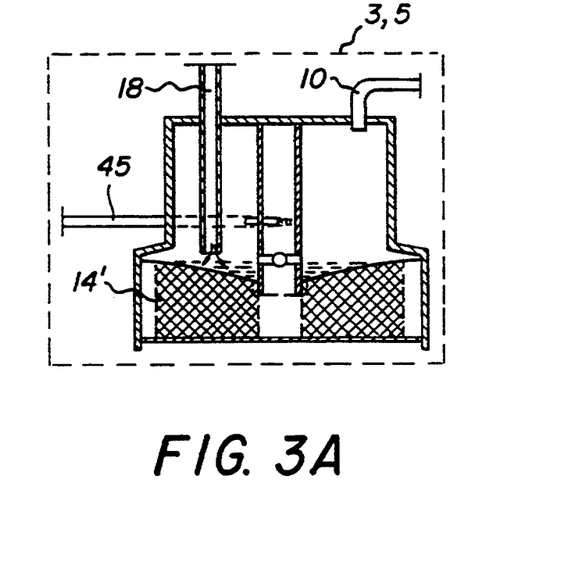
FIGS. 3A and 3B show enlarged portions of FIG. 3.

The apparatus shown in FIG. 3 basically corresponds to the apparatus shown in FIGS. 1 and 2 and those parts of FIG. 3 which are equivalent to the earlier described apparatus have been given the same reference numeral plus having a prim-index. The latter apparatus structurally differs from the earlier apparatus in that the separation and defoaming filter 3 and the de-airizing receiver are combined to a common unit as shown in greater detail in FIG. 3A. In this case the dosage agent is collected in a funnel formed container on top of the filter 14' in which the substance is mixed with the blood entering through the conduit 45. The blood enters the container 13' tangentially like a cyclone. After the blood has been filtered and defoamed the blood flows downwards along the walls of the container 13' through several successive collection pockets 47 having overflow walls 48 before the blood enters the drain conduit 31.

Figure 3B:
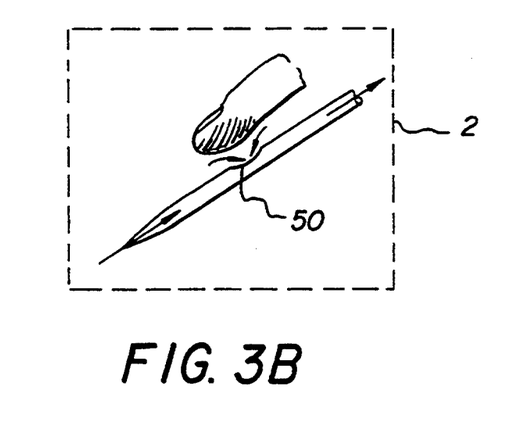

FIG. 3 also shows that a valve 49 can preferably be arranged adjacent the end of the suction nozzle 2, since it may happen that fragments get stuck at the point of the suction nozzle so that said nozzle becomes blocked. For preventing dosage agent from thereby being transmitted into the blood mixing part of the apparatus in case no blood is supplied it is important that the suction nozzle may easily be evacuated. The valve of the suction nozzle may for instance, as known, be formed as a finger hole 50 in the nozzle tube as shown in the detail picture of FIG. 3B.

We claim:

1. A method for sucking a gas-liquid mixture and for dosing the liquid of the gas-liquid mixture comprising the steps of:

generating a first negative pressure and a second negative pressure which is less negative than the first negative pressure but more negative than a third pressure at which the gas-liquid mixture is found;

connecting the second negative pressure to a suction hose having a suction nozzle to create a sucking pressure in the suction hose;

exerting the first negative pressure on an additive in a dosage container of a dosage device;

connecting the dosage container in which the additive contained directly to the suction hose through a connection device;

sucking up the gas-liquid mixture with the suction nozzle which causes a variation in the suction pressure in the suction hose depending on the amount of liquid being sucked up in the gas-liquid mixture; and dosing the additive to the gas-liquid mixture in the suction hose with the connection device in proportion to the amount of liquid sucked up through the suction hose which proportional dosing is caused by pressure differences between the first negative pressure exerted on the additive in the dosage container and the varying suction pressure in the suction hose.

2. A method for sucking and dosing as claimed in claim 1 wherein said dosage container connecting step includes the placing of a variable throttle valve in the connection device; and further including the step of adjusting the throttle valve to achieve a desired proportion of additive to sucked liquid.

3. A method for sucking and dosing as claimed in claim 1 and further including the steps of:
connecting an end of the suction hose remote from the suction nozzle to a filter;
filtering of the liquid of the gas-liquid mixture with the additive added in the filter;
passing the filtered liquid from the filter to a de-air receiver;
removing gas from the de-air receiver by connecting the de-air receiver to the second negative pressure;
collecting de-aired liquid at a bottom of the de-air receiver; and
draining of the de-aired liquid from the bottom of the de-air container into a closed container.

4. A method for sucking and dosing as claimed in claim 3 wherein said removing step includes the step of flowing the gas-liquid mixture along an inclined plane provided inside of the de-air receiver.

5. A method for sucking and dosing as claimed in claim 3 wherein said removing step includes the step of flowing the gas-liquid mixture along an inside wall of the de-air receiver.

6. A method for sucking and dosing as claimed in claim 3 and further including the steps of: initially de-contaminating the suction hose, the connection device, the filter, the de-air receiver, and the closed container; and subsequently reintroducing the collected liquid into a liquid system without contamination.

7. A method for sucking and dosing as claimed in claim 3 wherein said filtering step includes the steps of separating of any particles in the liquid of the gas-liquid mixture in the filter and disintegrating of any foam in the liquid of the gas-liquid mixture in the filter.

8. A method for sucking and dosing as claimed in claim 7:
wherein said draining step includes the step of exerting the first negative pressure on the closed container;
wherein the removing step includes the step of exerting the second negative pressure on the de-air receiver;
wherein the passing step includes the step of connecting the second negative pressure in the de-air receiver through the filter to the end of the suction hose;
and further including the step of regulating the first and second pressures relative to one another so that the pressure differences cause additive to be added to the gas-liquid mixture as soon as any amount of liquid is sucked through the suction hose but no additive will be conducted to the suction hose when no liquid is being sucked by the suction hose.

9. A method for sucking and dosing as claimed in claim 8 wherein said exerting step includes the steps of placing the additive in a flexible container, placing the flexible container in a second container, and connecting the first negative pressure to a space between the flexible container and the second container.

10. A method for sucking and dosing as claimed in claim 7 wherein said draining step includes the positioning of a displacement valve ball against a ball seat in a bottom of the de-air receiver and the selecting of a pressure differential between the first and second negative pressures such that a mass and lifting force of the valve ball causes the ball valve to be lifted up only when a predetermined amount of liquid is collected in the bottom of the de-air receiver and causes the ball valve to seat against the ball seat before the liquid in the de-air receiver is completely drained such that air is prevented from passing from the de-air receiver to the closed container.

11. A method for sucking and dosing as claimed in claim 8 wherein said draining step includes the positioning of a displacement valve ball against a ball seat in a bottom of the de-air receiver and the selecting of a pressure differential between the first and second negative pressures such that a mass and lifting force of the valve ball causes the ball valve to be lifted up only when a predetermined amount of liquid is collected in the bottom of the de-air receiver and causes the ball valve to seat against the ball seat before the liquid in the de-air receiver is completely drained such that air is prevented from passing from the de-air receiver to the closed container.

12. A device for sucking a gas-liquid mixture and for dosing the liquid of the gas-liquid mixture comprising:
a generating means for generating a first negative pressure and a second negative pressure which is less negative than the first negative pressure but more negative than a third pressure at which the gas-liquid mixture is found;
a suction hose having a suction nozzle;
a first conduit for connecting the second negative pressure to the suction hose to create a suction pressure in the suction hose such that sucking up of the gas-liquid mixture with the suction nozzle causes a variation in the suction pressure in the suction hose depending on the amount of liquid being sucked up in the gas-liquid mixture; and
a dosing means for dosing an additive to the gas-liquid mixture in the suction hose in proportion to the amount of liquid sucked up through the suction hose, said dosing means including
a dosage device including a dosage container in which the additive is contained,
an exerting means for exerting the first negative pressure on the additive in the dosage container, and
a second conduit for connecting the dosage container in which the additive is contained directly to the suction hose,
whereby proportional dosing of the additive from the dosage container to the suction hose is caused by pressure differences between the first negative pressure exerted on the additive in the dosage container and the varying suction pressure in the suction hose.

13. A device for sucking and dosing as claimed in claim 12 and further including:
a separation and defoaming filter to which the suction hose is connected, said filter including a filter container, a filter insert in the filter container which separates the filter container into an upper chamber in which incoming gas-liquid mixture with the additive added is received from the suction hose and a lower chamber in which filtrated and defoamed liquid is received after passing through the filter insert;

wherein said dosing means includes a variable throttle valve in the second conduit; and wherein said first conduit includes a connection of the second negative pressure to the lower chamber of the filter.

14. A device for sucking and dosing as claimed in claim 13 and further including a de-air receiver connected to the lower chamber of the filter in which the separated and defoamed liquid from the lower chamber is received; and wherein the first conduit further includes a connection of the second negative pressure to the de-air receiver such that the second negative pressure is conveyed from the de-air receiver through the filter to the suction hose.

15. A device for sucking and dosing as claimed in claim 14 and further including an air-void, flexible container bag; and wherein said de-air receiver includes:

(a) a flow means for flowing the liquid from the lower chamber of the filter slowly downwards therealong in the de-air receiver so that any air bubbles included in the liquid are evacuated through the connection of the second negative pressure to the de-air receiver, and (b) a valve means in a bottom of the de-air receiver for passing liquid collected in the bottom of the de-air receiver to the flexible container bag without the passage of any gas, said valve means including a level sensor means for opening the valve means only when a predetermined amount of liquid is present in the bottom of the de-air receiver and for closing the valve means before all of the liquid is passed to the flexible container bag so that no gas is passed to the flexible container bag.

16. A device for sucking and dosing as claimed in claim 15 and further including a rigid sealing casing in which the flexible container bag is received with a space therebetween, and a connection of the first negative pressure to the space between the rigid sealing casing and the flexible container bag; and wherein said valve means further including a valve cone and a valve seat on which the valve cone is seated.

17. A device for sucking and dosing as claimed in claim 16 wherein the valve cone is a displacement ball valve having a mass and a lifting force in the liquid, such that the valve ball is balanced by a pressure difference between the first and second negative pressures, the mass of the valve ball, and the lifting force of the valve ball.

18. A device for sucking and dosing as claimed in claim 17 wherein said generating means includes a negative pressure source and an adjustable pilot valve connected to the negative pressure source for creating the second negative pressure from the pressure source and for adjusting the pressure difference between the first negative pressure and the second negative pressure.

19. A device for sucking and dosing as claimed in claim 14 and further including a coating agent which makes the device blood compatible, the coating agent coating portions of the suction nozzle, the filter, the de-air receiver which contact the liquid.

20. A device for sucking and dosing as claimed in claim 12 wherein dosage device includes a rigid casing, wherein said dosage container is flexible and contained in the rigid casing, and wherein said exerting means is a connection of the first pressure to a space provided between the flexible dosage container and the rigid casing.

* * * * *